(12) United States Patent
Oogami (10) Patent No.: US 8,275,187 B2
(45) Date of Patent: Sep. 25, 2012

(54) RADIOGRAPHIC IMAGE DETECTION APPARATUS

(75) Inventor: Satoru Oogami, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 625 days.

(21) Appl. No.: 12/585,282

(22) Filed: Sep. 10, 2009

(65) Prior Publication Data

US 2010/0074505 A1 Mar. 25, 2010

(30) Foreign Application Priority Data

Sep. 24, 2008 (JP) .................................. 2008-244056

(51) Int. Cl.
*A61B 6/03* (2006.01)
(52) U.S. Cl. ........... 382/131; 378/62; 378/174; 378/208
(58) Field of Classification Search .................. 382/131; 378/62, 174, 205
See application file for complete search history.

(56) References Cited

U.S. PATENT DOCUMENTS

| | | | |
|---|---|---|---|
| 6,714,680 B1 * | 3/2004 | Sasada | 382/216 |
| 7,315,311 B2 * | 1/2008 | Sakai | 345/629 |
| 7,801,344 B2 * | 9/2010 | Wang | 382/128 |
| 2003/0048938 A1 * | 3/2003 | Wang et al. | 382/132 |
| 2007/0165141 A1 * | 7/2007 | Srinivas et al. | 348/571 |

FOREIGN PATENT DOCUMENTS

JP 2001-307085 11/2001

OTHER PUBLICATIONS

Kawashita et al., Collimation Detection in Digital Radiographs Using Plane Detection Hough Transformation, 2003, KES 2003, LNAI 2774, pp. 394-401.*

* cited by examiner

*Primary Examiner* — Toan Ton
*Assistant Examiner* — John Corbett
(74) *Attorney, Agent, or Firm* — Jean C. Edwards, Esq.; Edwards Neils PLLC

(57) ABSTRACT

In a radiographic image detection apparatus that can perform long-size radiography on a region of a patient that is larger than the detection range of a radiographic image detector, radiography is performed so that a collimator image is included in a radiographic image in such a manner that the collimator image is present in the vicinity of a side edge of the radiographic image. Further, the inclination of each radiographic image caused by inclination of the radiographic image detector at the time of radiography is corrected based on the collimator image. Further, a synthesis image is produced by combining the plurality of radiographic images the inclination of which has been corrected.

5 Claims, 5 Drawing Sheets

RADIOGRAPHIC IMAGE DETECTION APPARATUS

CROSS-REFERENCE TO RELATED APPLICATIONS

The present application claims priority from Japanese Patent Application No. 2008-244056, filed September 24, 2008, the contents of which are herein incorporated by reference in their entirety.

BACKGROUND OF THE INVENTION

1. Field of the Invention

The present invention relates to a radiographic image detection apparatus that can perform so-called long-size radiography, in which a plurality of radiographic images are combined to produce a single long-size radiographic image.

2. Description of the Related Art

Conventionally, in medical fields and the like, long-size radiography (longitudinal radiography) is performed in some cases. In the long-size radiography, a radiographic image detector is moved with respect to a subject (patient) to obtain radiographic images at a plurality of positions, and the obtained radiographic images are combined. Therefore, in the long-size radiography, it is necessary that the radiographic image detector can move for a long distance (range) (for example, 180 cm). However, if an accurate stage that does not shift nor rotate even if the radiographic image detector moves for such a long distance is adopted, the cost of the apparatus becomes very high. Therefore, the mechanism of moving the radiographic image detector is provided by an aluminum extrusion rail that also functions as a support pole, and a bearing in many cases. In such cases, a gap (interval, space or the like) is provided between the rail and the bearing so that the movement mechanism operates smoothly even if the aluminum extrusion rail is warped, bent or the like.

Especially, when long-size radiography is performed to obtain an image of the entire vertebral column (spinal column, backbone), a length or an angle between joints is measured. Therefore, highly accurate synthesis of the image is required, compared with ordinary radiography. Especially, a rotation error (inclination) with respect to an axis perpendicular to a detection plane (surface) of the radiographic image detector causes shifting of image-overlapping areas. Therefore, even higher accuracy is required for the rotation error, compared with other kinds of errors.

Therefore, a method for synthesizing an image based on markers provided in a radiographic image detector has been proposed so that a plurality of radiographic images can be combined even if mechanical shift in position, as described above, occurs (please refer to Japanese Unexamined Patent Publication No. 2001-307085 (Patent Literature 1), for example). In Patent Literature 1, markers that block radiation are provided at four corners of the radiographic image detector, and a radiographic image is obtained in such a manner that an image of the marker is included in the radiographic image. Further, rotation of a subject in a plurality of radiographic images is corrected based on images of the marker in the plurality of radiographic images.

However, in Patent Literature 1, it is necessary to arrange the markers in the vicinity of edges on both sides of the radiographic image detector so that the images of the markers are not substantially included in the radiographic images, in other words, so that the images of the markers are not present in the substantial areas of the radiographic images. Therefore, for example, even if a radiographic image of only the vertebral column of the subject needs to be obtained, the entire region of the subject with respect to the width direction needs to be irradiated with X-rays. Hence, there is a problem that the exposure dose of radiation to the patient with respect to the width direction becomes high.

SUMMARY OF THE INVENTION

In view of the foregoing circumstances, it is an object of the present invention to provide a radiographic image detection apparatus that can reduce the exposure dose of radiation to a subject (patient).

A radiographic image detection apparatus of the present invention is a radiographic image detection apparatus comprising:

a radiation source including a collimator that determines the irradiation range of radiation that is output to a subject;

a radiographic image detector that detects, as a radiographic image, the radiation that has been output from the radiation source and transmitted through the subject;

a detector movement means that moves the radiographic image detector parallel to a radiation detection surface;

an imaging control means that controls the collimator of the radiation source so that a collimator image that extends along the movement direction of the radiographic image detector is included in the radiographic image;

an image correction means that corrects the inclination of the radiographic image based on the collimator image in the radiographic image detected by the radiographic image detector; and an image synthesis means that produces a synthesis image by combining a plurality of radiographic images corrected by the image correction means.

Here, the type of the radiographic image detector is not particularly limited as long as the radiographic image detector detects, as a radiographic image, radiation that has passed through a subject. For example, the radiographic image detector may be a radiographic image detector of so-called TFT (thinfilm transistor) type. Alternatively, the radiographic image detector may be a radiographic image detector of so-called optical readout type.

Further, the structure of the collimator is not particularly limited as long as the collimator can determine the irradiation range. However, it is desirable that the collimator includes four linearly-formed collimator blades that move parallel and independently from each other to determine the irradiation range by the size of a closed space that is surrounded by the four collimator blades.

The image correction means should correct the inclination of the radiographic image based on the collimator image. For example, the image correction means may include an angle detection means and an image rotation means. Further, the angle detection means may detect an inclination angle between an edge portion of the collimator image and an edge of the radiographic image, and the image rotation means may rotate the radiographic image by the inclination angle detected by the angle detection means. At this time, the angle detection means may have a function of detecting the center of rotation of the radiographic image detector based on the position of the edge portion of the collimator image in the radiographic image.

Further, the image synthesis means may produce the synthesis image after the density characteristics of the plurality of radiographic images are adjusted so that the density characteristics become the same.

A radiographic image detection apparatus of the present invention is a radiographic image detection apparatus comprising:

a radiation source including a collimator that determines the irradiation range of radiation that is output to a subject;

a radiographic image detector that detects, as a radiographic image, the radiation that has been output from the radiation source and transmitted through the subject;

a detector movement means that moves the radiographic image detector parallel to a radiation detection surface;

an imaging control means that controls the collimator of the radiation source so that a collimator image that extends along the movement direction of the radiographic image detector is included in the radiographic image;

an image correction means that corrects the inclination of the radiographic image based on the collimator image in the radiographic image detected by the radiographic image detector; and an image synthesis means that produces a synthesis image by combining a plurality of radiographic images corrected by the image correction means.

Therefore, unlike conventional apparatuses, the radiographic image detection apparatus of the present invention can correct the inclination of a radiographic image and position (align) the radiographic image without irradiating a marker or markers located at an edge of a radiographic image detector with radiation. Hence, it is possible to reduce the exposure dose of radiation to the subject.

Further, when the image correction means includes an angle detection means and an image rotation means, and the angle detection means detects an inclination angle between an edge portion of the collimator image and an edge of the radiographic image, and the image rotation means rotates the radiographic image by the inclination angle detected by the angle detection means, it is possible to accurately detect the inclination angle by using the edge portion of the collimator image, the edge portion that is substantially linearly formed.

Further, when the angle detection means has a function of detecting the center of rotation of the radiographic image detector based on the position of the edge portion of the collimator image in the radiographic image, even if the center of the radiographic image detector is not the center of rotation, it is possible to accurately correct the inclination of the radiographic image.

Further, when the collimator includes four linearly-formed collimator blades that move parallel and independently from each other to determine the irradiation range by the size of a closed space that is surrounded by the four collimator blades, the inclination angle of the collimator image does not depend on the inclination of the collimator. Therefore, it is possible to accurately detect the inclination angle of the radiographic image detector per se to correct the rotation of the radiographic image.

Further, when the image synthesis means produces the synthesis image after the density characteristics of the plurality of radiographic images are adjusted so that the density characteristics become the same, it is possible to improve the image quality of the synthesis image produced by combining the plurality of radiographic images.

DESCRIPTION OF THE PREFERRED EMBODIMENTS

Figure 1:
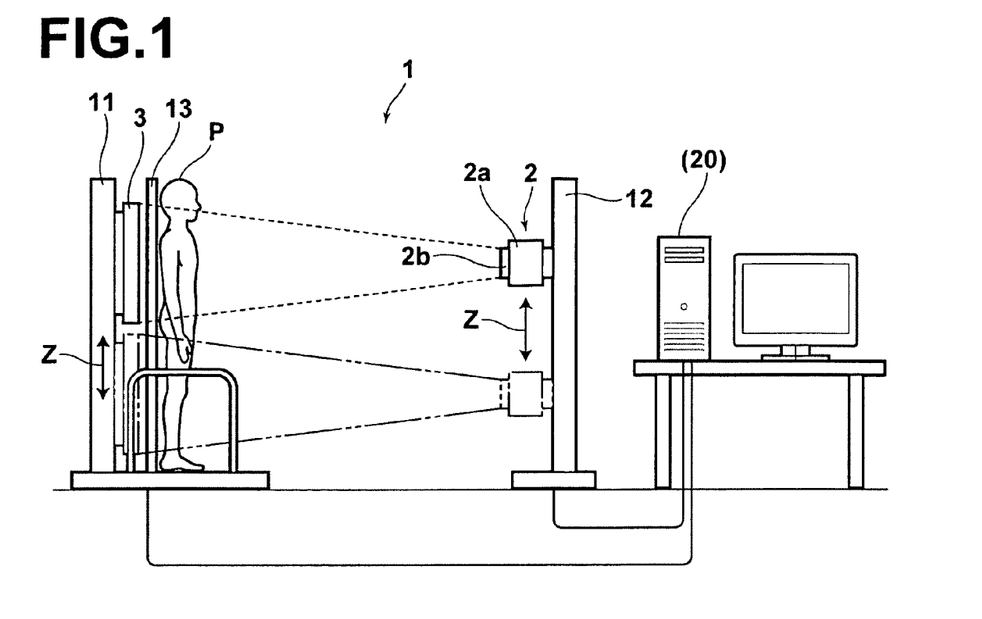
FIG. 1 is a schematic diagram illustrating an embodiment of a radiographic image detection apparatus of the present invention.

Hereinafter, embodiments of the present invention will be described in detail with reference to drawings. FIG. 1 is a schematic diagram illustrating a side view of a radiographic image obtainment system according to an embodiment of the present invention. A radiographic image detection apparatus 1 illustrated in FIG. 1 can perform two kinds of radiography, namely, so-called long-size radiography (longitudinal radiography) and ordinary radiography. In the long-size radiography, radiography is performed a plurality of times to obtain radiographic images of different regions of a subject. In the ordinary radiography, radiography is performed on a predetermined region of the subject. When the long-size radiography is performed, a screen 13 is attached to the radiographic image detection apparatus 1, and when the ordinary radiography is performed, the screen 13 is removed from the radiographic image detection apparatus 1.

Figure 2:
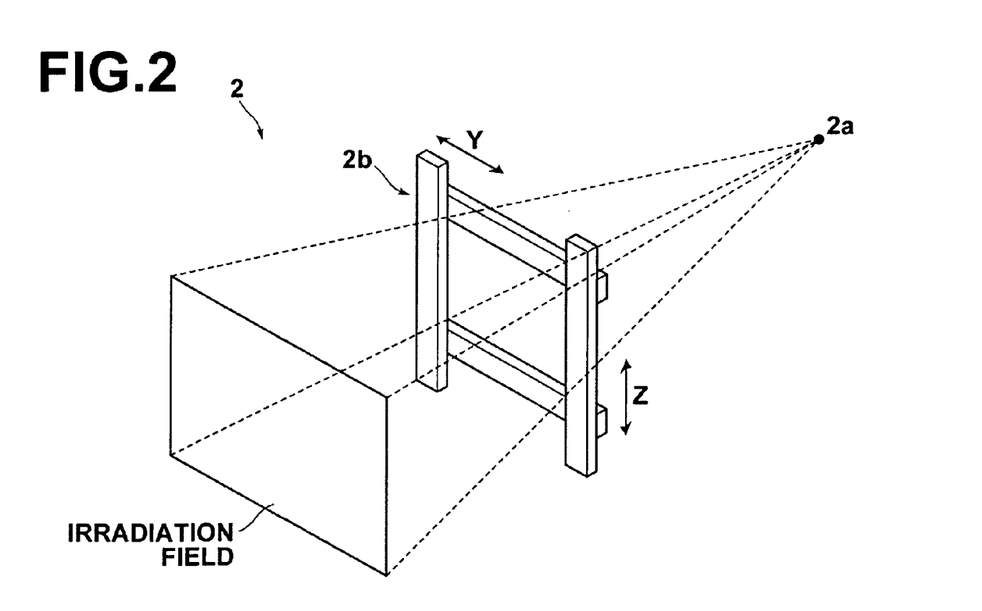
FIG. 2 is a schematic diagram illustrating an example of a radiation source in the radiographic image detection apparatus illustrated in FIG. 1.

The radiographic image detection apparatus 1 includes a radiation source 2, a radiographic image detector 3, an imaging control means 20, and the like. The radiation source 2 irradiates subject S with radiation. The radiation source 2 includes an X-ray tube 2a and a collimator 2b. FIG. 2 is a schematic diagram illustrating an example of the radiation source 2. The collimator 2b illustrated in FIG. 2 adjusts the irradiation range of radiation that is output from the X-ray tube 2a. For example, the collimator 2b includes four collimator blades (lead plates). Each of the four collimator blades moves independently from each other, and they move parallel in the direction of arrow Y or in the direction of arrow Z. The irradiation range of radiation is determined by a rectangular space enclosed by the collimator blades. Here, the collimator blades are linearly formed (in straight line form), as described above. Therefore, collimator image OC appears in a radiographic image (or included in the radiographic image) linearly extends (in straight line form) (please refer to FIGS. 4A and 4B).

Further, the movement of the collimator blades is controlled by the imaging control means 20. Especially, the collimator blades that extend in the direction of arrow Z are controlled so that they are positioned substantially parallel to the direction of arrow Z even if a tube ball rotates or the radiation source 2 per se moves parallel.

The radiographic image detector 3 illustrated in FIG. 1 stores, as a static latent image, radiographic image information represented by radiation that has passed through the subject S. Further, the static latent image stored in the radiographic image detector 3 is read out to detect the distribution of transmittance of radiation as a radiographic image. The configuration and structure of the radiographic image detector 3 is not limited as long as the radiographic image detector 3 can detect radiation and output the detected radiation as image information. For example, the radiographic image detector 3 may be a solid-state detector of TFT type, a solid-state detector of optical readout type and the like.

A detector movement means 11 moves the radiographic image detector 3 in a vertical direction (in the direction of arrow Z) along the detection surface. For example, the detector movement means 11 includes a rail and a drive means, such as a bearing and a motor. Meanwhile, a radiation source movement means 12 moves the radiation source 2 in the vertical direction (in the direction of arrow Z) so that the irradiation position of radiation is changed to correspond to the position of the radiographic image detector 3. In FIG. 1, the radiation source 2 is moved synchronously with the radiographic image detector 3 to change the irradiation position. Alternatively, the irradiation position of radiation may be changed by swinging the radiation source 2.

The imaging control means 20 illustrated in FIG. 1 controls the imaging operation (radiography operation) by the radiographic image detection apparatus 1. The imaging control means 20 automatically correlates the positions of regions of the subject S with the positions of the radiation source 2 and the radiographic image detector 3 based on information about the imaging range with respect to the subject S and information about an actual imaging range. Further, the imaging control means 20 controls each apparatus (device and unit) so that the subject is imaged at an optimum dose of radiation in each imaging (radiography). The imaging control means 20 controls imaging, for example, in such a manner that first imaging (radiography) is performed on the vicinity of the head of the subject S and the second imaging (radiography) is performed on the vicinity of the chest of the subject S. Further, the imaging control means 20 determines the radiation dose based on the control operation.

Figure 4A:
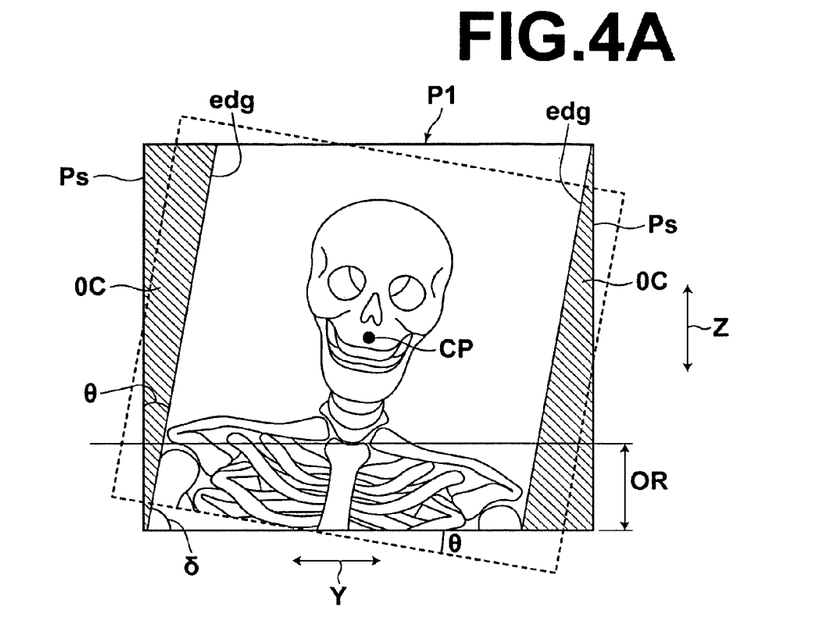
FIG. 4A is a schematic diagram illustrating an example a radiographic image detected when the radiographic image detector illustrated in FIG. 3 is inclined.
Figure 4B:
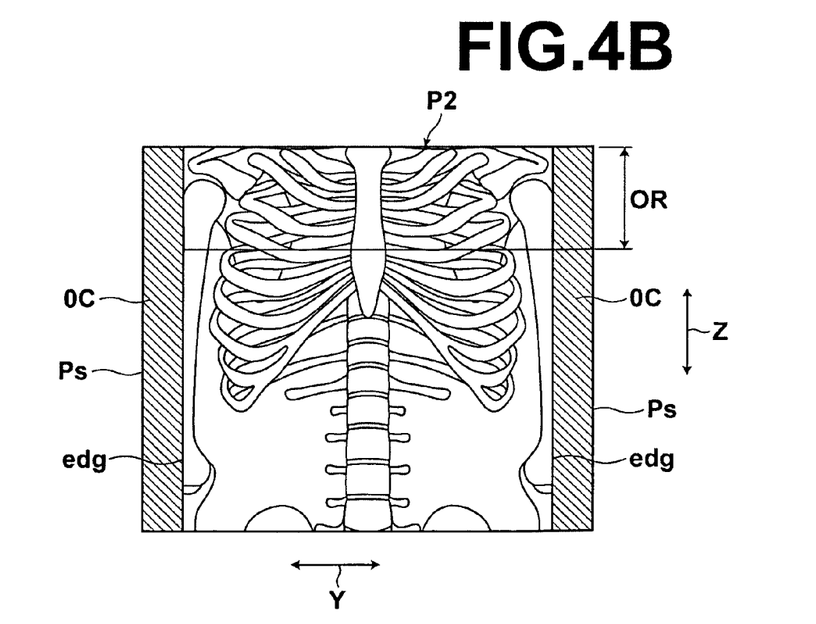
FIG. 4B is a schematic diagram illustrating an example a radiographic image detected when the radiographic image detector illustrated in FIG. 3 is not inclined.

Further, the imaging control means 20 has a function of controlling the operation of the collimator 2b so that the irradiation field of radiation output from the radiation source 2 does not exceed the width of the radiographic image detector 3. Accordingly, as illustrated in FIGS. 4A and 4B, a collimator image OC including edge portions edg appears. The edge portions edg extend substantially linearly along the movement direction (the direction of arrow Z) of the radiographic image detector 3, and the edge portions edg are present on both sides of the radiographic images P1 and P2.

Figure 3:
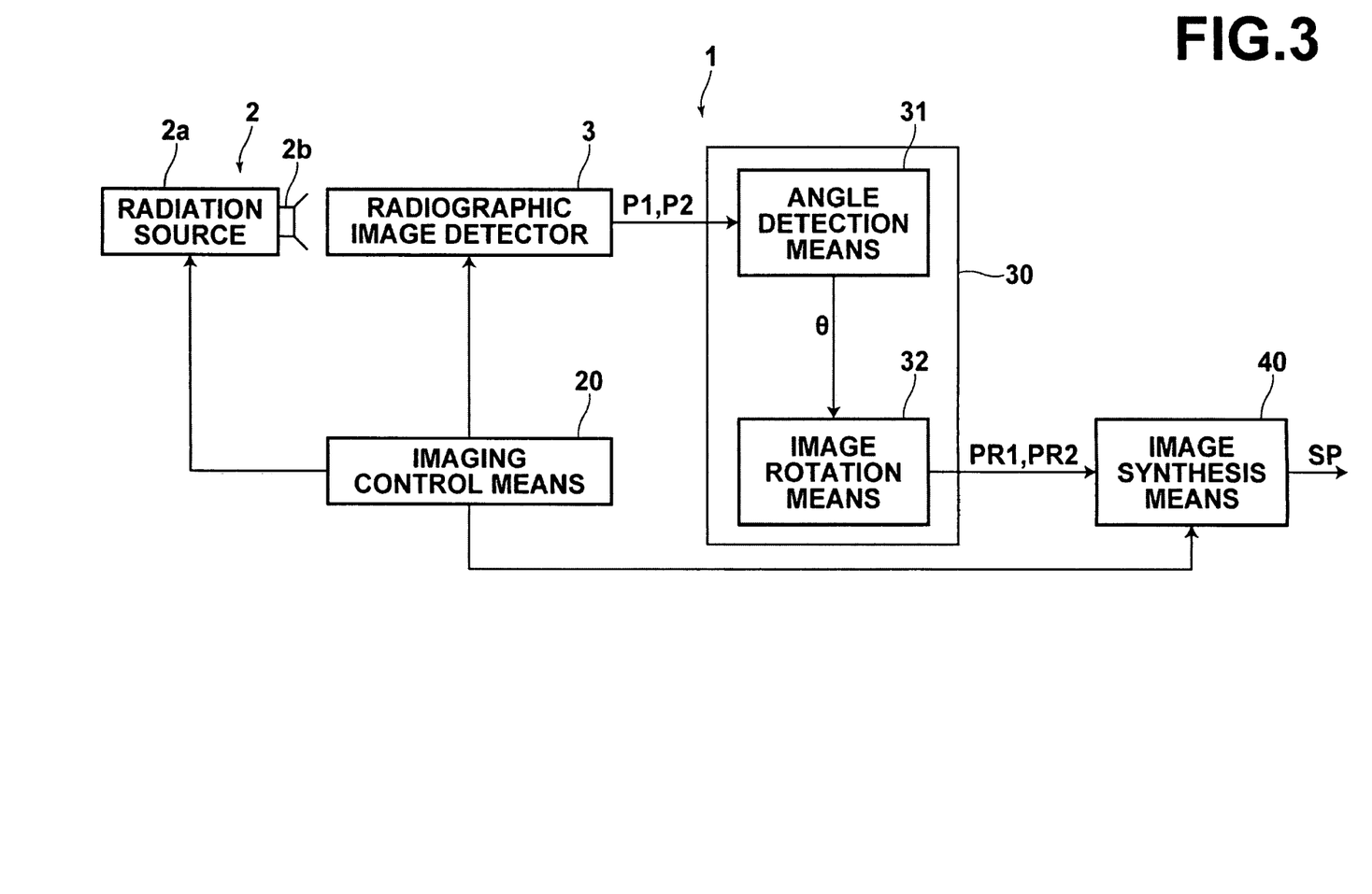
FIG. 3 is a block diagram illustrating an embodiment of a radiographic image detection apparatus of the present invention.

FIG. 3 is a block diagram illustrating an embodiment of a radiographic image detection apparatus of the present invention. The radiographic image detection apparatus 1 illustrated in FIG. 3 further includes an image correction means 30 and an image synthesis means 40. The image correction means 30 corrects inclination of the radiographic image based on the collimator image OC in the radiographic image detected by the radiographic image detector 3. The image correction means 30 includes an angle detection means 31 and an image rotation means 32.

The angle detection means 31 detects inclination angles θ between the edge portions edg of the collimator images OC and the edges (sides) Ps of the radiographic images P1 and P2. Here, when radiography is performed in a state in which the radiographic image detector 3 is rotated and inclined, the edge Ps of the radiographic image P is inclined with respect to the edge portion edg of the collimator image OC by the angle of θ, as illustrated in FIG. 4A. The angle detection means 31 detects the inclination angle θ. Meanwhile, as illustrated in FIG. 4B, when radiography is performed in a state in which the radiographic image detector 3 is not inclined by rotation, the edge Ps of the radiographic image P2 and the edge portion edge of the collimator image OC are substantially parallel to each other. Therefore, the angle detection means 31 detects the inclination angle of 0 (θ=0°).

The image rotation means 32 rotates the radiographic image P1 and P2 by the inclination angles θ detected by the angle detection means 31. Specifically, when the side edge Ps of the radiographic image P1 and the edge portion edg of the collimator image OC are inclined from each other by inclination angle θ, as illustrated in FIG. 4A, the image rotation means 32 rotates the radiographic image by −θ degrees to correct the image, and outputs radiographic image PR1 after correction. When the inclination angle is 0 (θ=0°), as illustrated in FIG. 4B, the image rotation means 32 outputs radiographic image PR2 without correcting the radiographic image P2.

For the purpose of explanation, in FIG. 4A, a case in which the center CP of rotation is located at the center of the radiographic image P1 is used as an example. However, the angle detection means 31 may detect center CP of rotation from the collimator image OC, and the image may be corrected by using the detected center CP of rotation and the inclination angle θ. Specifically, the inclination angle θ of the radiation source 2 or the detection image detector 3 is caused by the structure of the detector movement means (relationship between the rail and the bearing, or the like). Therefore, the center CP of rotation of inclination is not always located at the center of the radiographic image detector 3. When the center CP of rotation is shifted from the center of the radiographic image P1, the edge portions edg also shift in the direction of arrow Y or in the direction of arrow Z in the radiographic image P1 by the shift amount (shift of the center CP of rotation from the center of the radiographic image P1). Therefore, the angle detection means 31 can detect the center CP of rotation of inclination based on the position of the edge portion edg of the collimator image in the radiographic image P1. Further, the image correction means 30 rotates the radiographic image P1 with respect to the detected center CP of rotation by angle −θ, which corresponds to the inclination angle.

Figure 5:
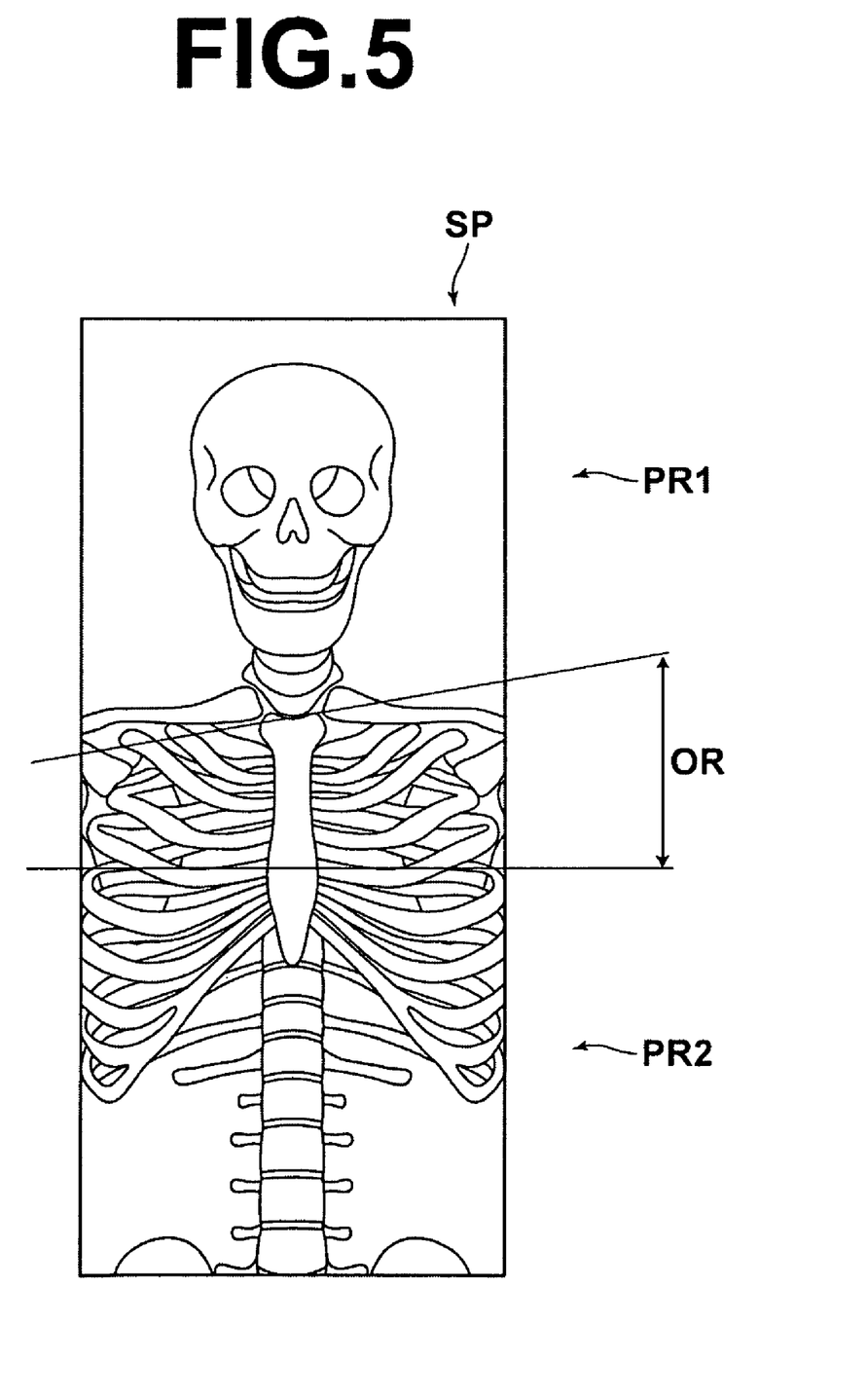
FIG. 5 is a schematic diagram illustrating an example of a synthesis image produced by an image synthesis means illustrated in FIG. 3.

The image synthesis means 40 illustrated in FIG. 3 combines a plurality of radiographic images P1 and P2 obtained during long-size radiography to generate a synthesis image SP, as illustrated in FIG. 5. Here, the image synthesis means 40 combines the plurality of radiographic images P based on the collimator images OC included in the radiographic images P. At this time, the plurality of radiographic images P1 and P2 are positioned by performing pattern matching line by line, and synthesis is performed at a position at which the correlation becomes the highest. Further, the image synthesis means 40 synthesizes overlap portion OR of images that are adjacent to each other by addition average processing. The synthesis processing is not limited to addition average processing. The processing may be performed by known image processing, such as weighted addition processing.

The image synthesis means 40 may have a function of adjusting the density characteristics of each of the radiographic images P1, P2 before synthesis. The density may be adjusted by using a known technique. For example, histograms are generated for the radiographic images P1 and P2, and automatic adjustment is performed, based on the histograms, so that the densities and contrasts of the images approximate to each other. At this time, the density or contrast of each image may be adjusted based on the density or contrast of a predetermined base image (for example, first image, which was obtained first in a series of images). Alternatively, a value may be set in advance as a base density or a base contrast, and the density or contrast of each of the images may be adjusted based on the set value. Further, the image synthesis means 40 may have a trimming function for removing the collimator image OC from the synthesis image SP.

As described above, the image processing means 30 performs positioning based on the collimator image OC in the radiographic image. Therefore, it is possible to reduce the exposure dose of radiation to the subject, compared with a conventional method of performing positioning by using markers. In the conventional radiographic image detector, the markers are provided at four corners so that they are not present in the region of interest. When an operator performs radiography in such a manner to include the markers in the radiographic image, even if the region of interest is located only in a central area of the radiographic image detector 3, it is necessary to irradiate the entire surface of the radiographic image detector 3 with radiation.

In contrast, when positioning is performed based on the collimator image OC, even if the irradiation field is set so that only the region of interest is irradiated with radiation, it is possible to perform accurate positioning. Therefore, for example, when long-size radiography (imaging) is performed on the spinal cord of the subject, it is not necessary to obtain the images of the markers by irradiating other regions of the subject, such as the ribs of the subject. Hence, it is possible to reduce the exposure dose of radiation to the subject.

Figure 6:
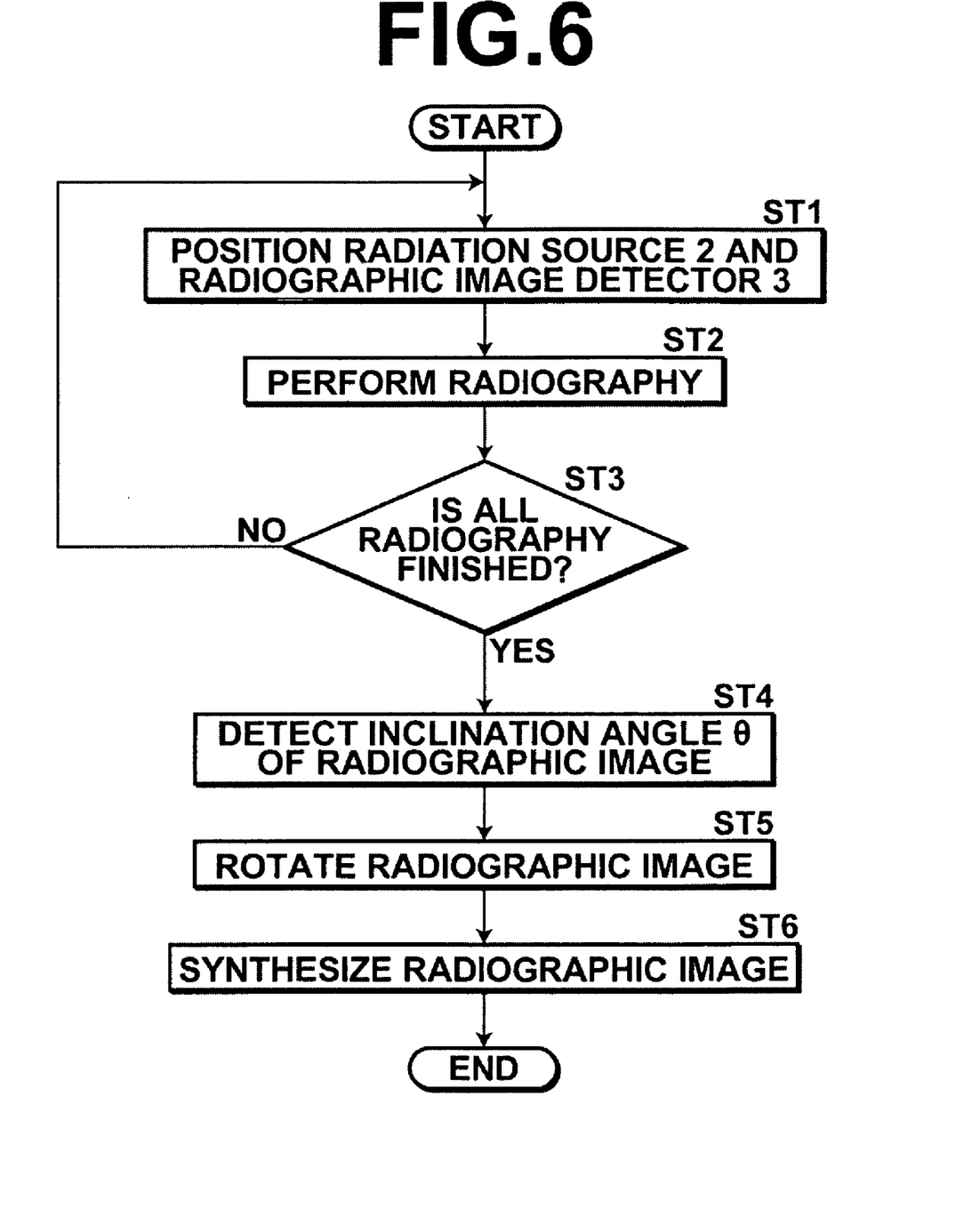
FIG. 6 is a flow chart showing an example of operations by the radiographic image detection apparatus of the present invention.

FIG. 6 is a flowchart showing an example of operations of a radiographic image detection apparatus of the present invention. The example of operations of the radiographic image detection apparatus will be described with reference to FIGS. 1 through 6. First, subject S stands in front of the screen 13, and the radiation source 2 and the radiographic image detector 3 are positioned (step ST1). Then, the subject S is irradiated with radiation output from the radiation source 2, and radiation that has passed through the subject S is detected, as a radiographic image, by the radiographic image detector 3 (step ST2). A predetermined number of times of radiography is performed while the positions of the radiation source 2 and the radiographic image detector 3 are changed to detect a plurality of radiographic images P1, P2 (step ST1 through step ST3).

Next, the angle detection means 31 of the image correction means 30 detects the inclination angle θ of each of the radiographic images P1, P2 caused by the inclination of the radiographic image detector 3 or the like (step ST4, please refer to FIGS. 4A and 4B). Further, the image rotation means 32 performs correction processing of rotating the radiographic images P1, P2 based on the detected inclination angles θ (step ST5). After then, the image synthesis means 40 combines a plurality of radiographic images PR1, PR2, the inclination of which has been corrected, to generate a long-size synthesis image SP (step ST6, please refer to FIG. 5).

According to the aforementioned embodiment of the present invention, the radiation source 2, the radiographic image detector 3, the detector movement means 11, the imaging control means 20, the image correction means 30, and the image synthesis means 40 are provided. Further, the radiation source 2 includes the collimator 2b that determines the irradiation range of radiation that irradiates the subject S. Further, the radiographic image detector 3 detects, as radiographic images P1, P2 including the images of the collimator 2b, radiation that has been output from the radiation source 2 and transmitted through the subject S. Further, the detector movement means 11 moves the radiographic image detector 3 parallel to the radiation detection surface (along the radiation detection surface). Further, the imaging control means 20 controls the collimator 2b in the radiation source 2 so that the collimator image OC of the collimator 2b that extends along the movement direction (direction of arrow Z) of the radiographic image detector 3 is included in the radiographic images P1, P2. Further, the image correction means 30 corrects the inclination of the radiographic images P1, P2 based on the collimator images OC in the radiographic images P1, P2 detected by the radiographic image detector 3. Further, the image synthesis means 40 generates a synthesis image SP by combining the plurality of radiographic images P1, P2 that have been corrected by the image correction means 30. Therefore, unlike conventional apparatuses, it is possible to correct the inclination of the radiographic image and to perform positioning without irradiating markers that are located at edges (corners) of the radiographic image detector 3. Hence, it is possible to reduce the exposure radiation dose to the subject with respect to the width direction.

Further, as illustrated in FIG. 3, when the image correction means 30 includes the angle detection means 31 that detects the inclination angle θ between the edge portions edg of the collimator image OC and the edges (sides) of the radiographic images P1, P2 and the image rotation means 32 that rotates the radiographic images P1, P2 by the inclination angles θ detected by the angle detection means 31, it is possible to accurately detect the inclination angles θ by using the edge portions edg of the collimator image OC. The edge portions edg are substantially linearly formed.

Further, when the angle detection means 31 has a function of detecting the center CP of rotation of the radiographic image detector 3 based on the position of the edge portion edg of the collimator image OC in the radiographic image P1, even if the center of the radiographic image detector 3 is not the center CP of rotation, it is possible to accurately correct the inclination of the radiographic image P1.

Further, as illustrated in FIG. 2, when the collimator 2b includes four linearly-formed collimator blades that move parallel and independently from each other, and the irradiation range is determined by the size of a closed space enclosed (surrounded) by the four collimator blades, the inclination angle θ of the collimator image OC does not depend on the inclination of the collimator 2b. Therefore, it is possible to accurately detect the inclination angle θ of the radiographic image detector 3 per se and to correct the rotation of the radiographic image P1.

Further, when the image synthesis means 40 illustrated in FIG. 3 combines the radiographic images P1, P2 after the density of each of the radiographic images P1, P2 is adjusted so that they have the same density characteristics, it is possible to improve the image quality of the synthesis image SP obtained by combining the plurality of radiographic images P1, P2.

The embodiment of the present invention is not limited to the aforementioned embodiments. For example, in FIG. 3, a case in which the collimator image OC is included in the radiographic image so that the collimator image OC is present at either side edge of the radiographic image is used as an example. However, if the collimator image OC is present at least at a side edge of the radiographic image, the image correction means 30 can correct the inclination.

Further, in FIGS. 4A, 4B and 5, a case in which the synthesis image SP is generated by using two radiographic images P1, P2 is used as an example. Alternatively, the synthesis image may be generated by using two or more radiographic images.

What is claimed is:

1. A radiographic image detection apparatus comprising:
a radiation source including a collimator that determines the irradiation range of radiation that is output to a subject;
a radiographic image detector that detects, as a radiographic image, the radiation that has been output from the radiation source and transmitted through the subject;
a detector movement means that moves the radiographic image detector parallel to a radiation detection surface;
an imaging control means that controls the collimator of the radiation source so that a collimator image that extends along the movement direction of the radiographic image detector is included in the radiographic image;
an image correction means that corrects the inclination of the radiographic image based on the collimator image in the radiographic image detected by the radiographic image detector; and
an image synthesis means that produces a synthesis image by combining a plurality of radiographic images corrected by the image correction means.

2. A radiographic image detection apparatus, as defined in claim 1, wherein the image correction means includes an angle detection means and an image rotation means, wherein the angle detection means detects an inclination angle between an edge portion of the collimator image and an edge of the radiographic image, and wherein the image rotation means rotates the radiographic image by the inclination angle detected by the angle detection means.

3. A radiographic image detection apparatus, as defined in claim 2, wherein the angle detection means has a function of detecting the center of rotation of the radiographic image detector based on the position of the edge portion of the collimator image in the radiographic image.

4. A radiographic image detection apparatus, as defined in claim 1, wherein the collimator includes four linearly-formed collimator blades that move parallel and independently from each other to determine the irradiation range by the size of a closed space that is surrounded by the four collimator blades.

5. A radiographic image detection apparatus, as defined in claim 1, wherein the image synthesis means produces the synthesis image after the density characteristics of the plurality of radiographic images are adjusted so that the density characteristics become the same.

* * * * *